United States Patent
Berlinger et al.

(10) Patent No.: US 10,413,752 B2
(45) Date of Patent: Sep. 17, 2019

(54) X-RAY PATIENT POSITION MONITORING

(71) Applicant: Brainlab AG, Munich (DE)

(72) Inventors: Kajetan Berlinger, Munich (DE); Jorg Rehs, Munich (DE)

(73) Assignee: BRAINLAB AG, Munich (DE)

( * ) Notice: Subject to any disclaimer, the term of this patent is extended or adjusted under 35 U.S.C. 154(b) by 124 days.

(21) Appl. No.: 15/549,091

(22) PCT Filed: Feb. 9, 2015

(86) PCT No.: PCT/EP2015/052607
§ 371 (c)(1),
(2) Date: Aug. 4, 2017

(87) PCT Pub. No.: WO2016/128014
PCT Pub. Date: Aug. 18, 2016

(65) Prior Publication Data
US 2018/0021597 A1 Jan. 25, 2018

(51) Int. Cl.
*A61N 5/10* (2006.01)

(52) U.S. Cl.
CPC ......... *A61N 5/1049* (2013.01); *A61N 5/1067* (2013.01); *A61N 2005/1051* (2013.01);
(Continued)

(58) Field of Classification Search
CPC ............... A61N 5/1049; A61N 5/1067; A61N 2005/1062; A61N 2005/1051;
(Continued)

(56) References Cited

U.S. PATENT DOCUMENTS

| 5,207,223 A | 5/1993 | Adler |
| 6,865,253 B2 | 3/2005 | Blumhofer et al. |
| 2004/0092815 A1* | 5/2004 | Schweikard ............. A61B 6/12 600/425 |
| 2007/0291895 A1 | 12/2007 | Yin et al. |
| 2009/0129556 A1* | 5/2009 | Ahn .......................... A61B 6/04 378/208 |

(Continued)

FOREIGN PATENT DOCUMENTS

| WO | WO9802091 A1 | 1/1998 |
| WO | WO2005024721 A2 | 3/2005 |
| WO | WO2011116830 A1 | 9/2011 |

OTHER PUBLICATIONS

Roth, et al. "Fast and Precise 2D/3D Intensity-Based Fusion of Fluoroscopic Images with CT—AN objective Evaluation Using Gold Standard Datasets" Curac. 2004.
(Continued)

*Primary Examiner* — Daniel G Mariam
(74) *Attorney, Agent, or Firm* — Middleton Reutlinger (57) ABSTRACT

A data processing method performed by a computer for monitoring the position of a patient, comprising the steps of: acquiring a 3D image dataset of the patient; acquiring an initial real image of the patient from a medical imaging system having a known and fixed location in space, thus defining a known viewing direction of the initial real image in space, the real image being taken at a first point in time; —performing 2D/3D registration by calculating a simulated image from the 3D image dataset which matches the initial real image best, the simulated image having a viewing direction onto the 3D image dataset; storing an initial similarity measure value for the pair of the initial real image and the calculated simulated image; —acquiring a subsequent real image from the medical imaging system taken at a second point in time later than the first point in time;

(Continued)

calculating a subsequent similarity measure value for the pair of the subsequent real image and the calculated simulated image; and outputting an indication signal if the difference between the initial similarity measure value and the subsequent similarity measure value fulfills a predetermined criterion.

15 Claims, 3 Drawing Sheets

(52) U.S. Cl.
CPC ............. *A61N 2005/1058* (2013.01); *A61N 2005/1062* (2013.01)

(58) Field of Classification Search
CPC .... A61N 2005/1058; A61N 2005/1072; G06T 2207/10124

USPC ........................................................ 382/154
See application file for complete search history.

(56) References Cited

U.S. PATENT DOCUMENTS

| 2010/0080354 | A1* | 4/2010 | Fu ..................... A61N 5/1049 378/65 |
| 2010/0246915 | A1 | 9/2010 | Yamakoshi et al. |
| 2013/0188856 | A1 | 7/2013 | Adler, Jr. et al. |

OTHER PUBLICATIONS

International Search Report and Written Opinion for PCT/EP2015/052607 dated Oct. 22, 2015.

* cited by examiner

X-RAY PATIENT POSITION MONITORING

The present invention relates to a data processing method, performed by a computer, for monitoring the position of a patient and to a corresponding computer program and system.

The present invention has been made in the environment of the ExacTrac® system of the applicant. This system is used for radiotherapy and radiosurgery treatments and irradiates a particular target region within a patient with a treatment beam which is generated by a treatment beam generator. The treatment beam generator can rotate, such that the treatment beam also rotates within a plane. During this rotation, a particular area relative to the ExacTrac® system is always irradiated when the treatment beam is on, while all other areas are only irradiated temporarily. The always irradiated area is called the isocenter of the apparatus. For the treatment, the area to be treated in the patient, which is also referred to as target region, should be at the same position as the isocenter of the apparatus.

The ExacTrac® apparatus comprises two X-ray devices with a known position in space. Before and/or during the treatment, the position of the patient relative to the apparatus is verified from the X-ray images taken by the X-ray devices. The present invention relates to a simple verification (also referred to as monitoring) of the patient's position relative to the apparatus, and preferably a verification which can be performed in real time.

The basic idea of the present invention is to acquire a 3D image of a patient. In addition, a first X-ray image of the patient when he or she is in a desired position relative to the apparatus is acquired. In a next step, a DRR image is calculated from the 3D image which matches the X-ray image as exactly as possible. Later during the treatment, a new X-ray image is acquired and compared to the DRR image. If the difference between the DRR image and the new X-ray image is larger than the difference between the DRR image and the first X-ray image by a predetermined margin, then it is assumed that the patient has moved.

It shall be noted that the present invention is applicable to other scenarios beyond the ExacTrac® system. It can even utilize other kinds of images, such as photographic images or ultrasound images, instead of the X-ray images and corresponding synthesized images calculated from a 3D image instead of the DRR image.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a data processing method performed by a computer for monitoring the position of a patient.

The method involves the step of acquiring a 3D image dataset of a patient. The 3D image dataset represents a 3D image of the patient. The 3D image of the patient does not necessarily depict the whole patient, but may be limited to a part of the patient. The imaged part of the patient preferably comprises a particular body structure of the patient, such as a tumor to be treated, or a part which has an invariant position relative to the body structure. The 3D image is preferably taken before the actual treatment begins and is for example a 3D image which is used to plan the treatment.

The method further involves the step of acquiring an initial real image of the patient from a medical imaging system having a known and fixed location in space, thus defining a known viewing direction of the initial real image in space. The real image is taken at a first point in time. A real image is an image which is captured by the medical imaging system using a suitable imaging modality. In the case of an X-ray imaging system, the viewing direction is defined by the position of an X-ray source of the X-ray imaging system. The viewing direction can optionally further be defined by the position of an X-ray detector of the X-ray imaging system. In the case of an ultrasound image, the viewing direction of the initial real image is defined by the position of the ultrasound source.

In this document, the expression "viewing direction" does preferably not only refer to an orientation, but also to a location. A viewing direction of a real image is defined by the position of the imaging system which is used to generate the image in space.

In this document, the word "position" defines a spatial location in up to three spatial dimensions and/or an alignment in up to three rotational dimensions.

The initial real image of the patient is preferably taken when the patient is in a desired position (which is also referred to as initial position), for example relative to an operating room or a medical apparatus, like an apparatus which performs the present invention. In analogy to the 3D image described above, the real image may also depict only a part of the patient. Preferably, the initial real image and the 3D image dataset represent the same part of the patient or overlapping parts of the patient. The 3D image might be taken at, before or after the first point in time. Preferably, the 3D image was taken by use of the same modality as the initial real image.

The method further involves the step of performing 2D/3D registration by calculating a simulated image from the 3D image dataset which matches the initial real image best, the simulated image having a viewing direction onto the 3D image dataset. A simulated image is an image which is calculated from the 3D image dataset for a particular viewing direction onto the 3D image dataset. The best match is typically achieved if the viewing direction of the simulated image onto the 3D image dataset representing the patient is identical to the viewing direction of the initial real image onto the patient. In the following, the simulated image which matches the initial real image best is also referred to as best matching simulated image.

In the case of a simulated image, the 3D image dataset is a virtual imaged object which is imaged by a virtual imaging system. In other word, a simulated image is obtained by virtually imaging the 3D image dataset with a virtual imaging system. Contrary to the viewing direction of a real image, the viewing direction of a simulated image is the relative position between the 3D image dataset and the virtual imaging system. If the virtual imaging system and the 3D image dataset have a known position in space, a corresponding viewing direction of the simulated image results.

In theory, the 2D/3D registration can result in a simulated image which is exactly identical to the initial real image. However, effects such as noise may cause the simulated image and the initial real image to be different. Known 2D/3D registration methods therefore maximize the similarity between the simulated image and the initial real image.

The similarity is judged by use of a particular algorithm, which may depend on the kinds of image to be registered and typically results in a (single) similarity measure value. Typical 2D/3D registration approaches calculate a plurality of simulated images for different viewing directions onto the 3D image dataset, calculate the respective similarity measure values for the respective pairs of one of the simulated images and the initial real image and then vary the viewing direction onto the 3D image dataset until the similarity measure value is maximized.

The method further involves the step of storing an initial similarity measure value for the pair of the initial real image and the calculated simulated image. This initial similarity measure value is used as a reference for the subsequent monitoring.

The method further involves the step of acquiring a subsequent real image from the medical imaging system taken at a second point in time later than the first point in time. If the patient has not moved relative to the medical imaging system between the first and second points in time, then the simulated image and the subsequent real image are typically identical. The second point in time preferably is during treatment of the patient. The first point in time preferably is at the beginning of a treatment of the patient.

The method further involves calculating a subsequent similarity measure value for the pair of the subsequent real image and the calculated simulated image. If the patient has not moved between the first and second points in time, then the subsequent similarity measure value is (basically) equal to the initial similarity measure value, because the viewing direction of the subsequent real image onto the patient is the same as the viewing direction of the simulated image onto the 3D image dataset which represents the patient.

The method further involves the step of outputting an indication signal if the difference between the initial similarity measure value and the subsequent similarity measure value fulfils a predetermined criterion. In one embodiment, the predetermined criterion is that the difference equals or exceeds a particular threshold value. If the predetermined criterion is fulfilled, this means that the initial real image and the subsequent real image differ from each other by more than a predetermined margin, which may be interpreted as meaning that the patient has moved relative to the medical imaging system, and therefore for example relative to a treatment beam generator of the radiotherapy or radiosurgery system.

An advantage of the present invention is that determining whether or not the patient has moved between the first and second points in time does not require to perform an additional 2D/3D registration between the 3D image dataset and the subsequent real image and to then analyze the viewing directions of the simulated images of the two 2D/3D registrations. According to the present invention, a simple comparison between two 2D images is performed.

An image, such as an initial real image, a subsequent real image or a simulated image is preferably represented by a corresponding image dataset. The 3Dimage dataset represent a three-dimensional image of the patient.

In one embodiment, the steps of acquiring the subsequent real image, calculating a subsequent similarity measure value and outputting an indication signal are repeated periodically, for example with a frequency of 0.1 Hz, 0.2 Hz, 0.5 Hz, 1 Hz, 2 Hz, 5 Hz or 10 Hz. In addition or alternatively, the timing at which those steps are repeated depends on energy data which comprise information which describes (at least one) energy value which depends on the radiation energy applied to the patient's body. The steps are for example repeated if a particular radiation dose is applied to the patient. Details of determining the energy data are disclosed in the document WO2011/116830 A1.

In the description as given so far, the method uses a single initial real image, a single best-matching simulated image and a single subsequent real image. However, the method may equally utilize two or more real images (two or more initial real images and two or more subsequent real images), which results in a corresponding number of simulated images. This applies in particular if the invention is performed in the environment of a medical apparatus, such as an ExacTrac® system, which comprises two or more medical imaging systems having known and fixed locations in space. The use of two or more real images is explained below.

In one embodiment, a plurality of initial real images of the patient is acquired from a plurality of medical imaging systems having a known and fixed location in space, thus defining known viewing directions of the initial real images in space. The plurality of real images are taken at the first point in time. Performing 2D/3D registration then involves calculating a plurality of simulated images from the 3D image dataset which match the initial real images best, wherein there is one simulated image for each of the initial real images and each simulated image has a viewing direction onto the 3D image dataset. There is thus a plurality of pairs, each pair comprising an initial real image and corresponding simulated image.

Accordingly, a plurality of initial similarity measure values is stored, wherein there is one similarity measure value for each pair of an initial real image and a corresponding simulated image. Then a plurality of subsequent real images is acquired from the plurality of medical imaging systems. The subsequent real images are taken at the second point in time. The number of subsequent real images preferably equals the number of initial real images and the number of simulated images.

Then a plurality of subsequent similarity measure values is calculated for each pair of a subsequent real image and the corresponding calculated simulated image. A corresponding calculated simulated image is simulated image which corresponds to the initial real image which was captured using the same medical imaging system as the subsequent real image.

Finally, the indication signal is output if a value which is calculated from the differences between the initial similarity measure values and the corresponding subsequent similarity measure values fulfills a predetermined criterion.

In general, the viewing directions of the plurality of simulated images onto the 3D image dataset can be arbitrary if the 2D/3D registration is performed independently for each of the initial real images. However, it is preferable that the relations between the viewing directions of the simulated images equal the relations between the viewing directions of the real images. In other words, the viewing directions of the simulated images emulate the viewing directions of the real images. This results in the simulated images being consistent with the initial real images. In other words, the simulated images are calculated for a virtual set of medical imaging systems having the same arrangement as the set of real medical imaging systems.

Said value which defines whether or not the indication signal is output is calculated from all the differences (between the initial and the corresponding subsequent similarity measure values) or a subset of the differences. This value can also be referred to as overall difference. If the overall difference is calculated from all the differences, then the overall difference can for example be the sum or a (weighted) average of the differences. If the overall difference value is calculated from a subset of the differences, then the overall difference value can for example be the sum or a (weighted) average of the subset of the differences. Calculating the value only from a subset of the differences is for example advantageous if the field of view of one or more of the medical imaging systems is blocked, for example by a gantry which rotates a treatment beam generator of a radiotherapy or radiosurgery system. A difference corresponding to such a medical imaging system is preferably excluded from the overall difference value.

In one embodiment, the real image is an X-ray image and the simulated image is a DRR image. A DRR image is a digitally reconstructed radiograph image which is reconstructed (that is simulated or calculated) from a three-dimensional CT (computed tomography) image. A virtual X-ray imaging system is assumed and the CT image is at least partly provided in its field of view. The propagation of a virtual X-ray beam through the CT image is calculated, thus resulting in a simulated X-ray image. If the CT image exactly represents the patient and the viewing direction of the virtual X-ray imaging system onto the CT image exactly equals the viewing direction of a real X-ray imaging system onto the patient, the DRR (theoretically) exactly equals the real X-ray image as taken by the real X-ray imaging system.

As already indicated above, the real image might also be an image of another modality, such as for example an optical image or an ultrasound image. The simulated image then preferably is a simulated image of the same modality. The simulated image can for example be calculated from a 3D image dataset which represents a 3D ultrasound image or a 3D optical image of the patient. However, mixed modalities are possible. This means that the simulated image might be of a different modality than the real image or the simulated image might be calculated from a 3D image of a different modality. In one example, the simulated image is a DRR image which is calculated from a 3D MR (magnetic resonance) image.

In one embodiment, the 2D/3D registration involves positioning the 3D image dataset in space, wherein the position of the virtual imaging system for calculating the simulated image equals the position of the corresponding medical imaging system in space. In other words, a virtual medical imaging system is virtually placed in space at a position identical to the real medical imaging system. A position of the 3D image dataset in space is then adjusted, which means that the viewing direction of a simulated image onto the 3D image dataset is adjusted, until the simulated image matches the initial real image best. With the position of the virtual imaging system being fixed in space, the 2D/3D registration results in virtual position of the 3D image dataset in space which equals the position of the patient in space at the first point in time.

This is advantageous if a particular target position of the patient in space is defined, for example by a treatment plan. In the case of for example radiosurgery or radiotherapy, a treatment plan is typically based on the 3D image dataset in order to define a particular target area of the patient to be irradiated. In order to actually irradiate this area with a medical apparatus, the target area must be located at a particular position in space, that is a particular position relative to the medical apparatus. If the position of the 3D image dataset in space is known after the 2D/3D registration, the position of the target area, which is also referred to as isocenter, of the 3D image dataset is also known.

It shall be noticed that the isocenters of the medical apparatus and the 3D image dataset might not be identical in the initial position of the patient. A reason for this difference can be that the isocenter in the 3D image dataset might actually differ from the target area in the patient or other constraints prevent to make the isocenters of the medical treatment beam and the 3D image dataset to be equal. Another reason can be that a patient positioning system was used for positioning the patient, the positioning system using alternative criteria for positioning the patient. However, the initial position is assumed to be the position in which the patient should be during the treatment, and is therefore used as a reference for the monitoring according to the present invention.

In one embodiment, the 2D/3D registration is an iterative process starting with an initial position of the 3D image dataset in space. As outlined above, the 2D/3D registration typically involves calculating a plurality of simulated images and to maximize the similarity between the simulated images and the real image until the registration is found. In order to optimize the registration algorithm, the simulated images are not calculated over the complete range of viewing directions, which is defined by a six-dimensional space comprising three spatial and three rotational dimensions, but is limited to a particular range around the initial position of the 3D image dataset, which means an initial viewing direction. In this embodiment, this initial position is a position in which an isocenter defined with respect to the 3D image dataset equals an isocenter of a medical treatment beam. For the 2D/3D registration, it is thus assumed that the patient is already in the perfect position for the treatment. The 2D/3D registration therefore only calculates the difference between the actual position of the 3D image dataset (which equals the actual position of the patient in space) after the 2D/3D registration and the initial position of the 3D image dataset in space.

Preferably, the difference between the initial position of the 3D image dataset and the adjusted position of the 3D image dataset is stored as an offset. The offset then defines the difference between the initial position of the patient in space at the first point in time and a modified initial position of the patient in space in which the target area in the patient, which corresponds to the isocenter defined with respect to the 3D image dataset, is displaced relative to the isocenter of the medical treatment beam.

In one exemplary embodiment, if the position of the patient has been changed since the first point in time, new initial real images are acquired. A new 2D/3D registration is performed with an initial position of the 3D image dataset which is calculated from the offset and the change in the patient's position. A new initial similarity value is then stored. The change in the patient's position is typically known, for example if the patient's position was changed by one or more motors which drive a couch on which the patient lies. Instead of starting the new 2D/3D registration from scratch, an initial position of the 3D image dataset can be calculated by taking the previous position of the 3D image dataset in space, subtracting the offset from the previous position, relocating the 3D image dataset by the same relative position as the change in the patient's position and then adding the offset again.

In one embodiment, the calculated simulated image is stored for the subsequent calculation of the subsequent similarity measure value. However, in an alternative embodiment, the calculated simulated image is a re-calculated simulated image which is calculated from the 3D image dataset and the offset before the subsequent similarity measure value is calculated. This requires less storage space since no simulated image has to be stored, but on the other hand requires computational efforts to re-calculate the simulated image.

In one embodiment, a treatment beam is stopped if the indication signal is output. Since the indication signal indicates a movement of the patient by more than an allowed margin, the indication signal at the same time indicates that the treatment beam would no longer irradiate the target area. The treatment beam can then be stopped automatically as a precaution.

In one embodiment, a new 2D/3D registration is performed if the indication signal is output. As explained above, the calculation which decides whether or not the indication signal is to be output can be calculated in real time, while a 2D/3D registration is typically too complex to be performed in real time. However, a new 2D/3D registration is not necessary if the patient has not moved. So in this embodiment, a new 2D/3D registration is only performed if the indication signal is output, that is if the patient has moved.

Optionally, a new 2D/3D registration can be performed, for example in the background, even if no indication signal was output. However, completion of this 2D/3D registration is not necessary to determine whether the patient has moved or not.

In the description as given so far, (a) simulated image(s) which best match(es) the initial real image(s) has been used. However, situations might occur in which no indication signal is output even if the patient has moved. This might for example occur if the field of view of the medical imaging system is small and/or the simulated image is invariant to a particular change in the viewing direction, such as a rotation. In this case, embodiments which additionally utilize "non-perfect" simulated images, which also exhibit a particular similarity measure value with the real image, are advantageous.

In one embodiment, the method further involves a step of calculating an additional initial similarity measure value for a pair of the initial real image and an additional simulated image having a viewing direction which differs from the viewing direction of the best matching simulated image by a known difference. The method of this embodiment then involves calculating an additional subsequent similarity measure value for a pair of the subsequent real image and the additional simulated image. The method of this embodiment then further involves including the additional similarity measure value when calculating the initial similarity measure value. This means that the initial similarity measure value which is calculated for the pair of the initial real image and the best matching simulated image is modified by the additional initial similarity measure, for example by calculating the sum or a (weighted) average.

The method of this embodiment further involves including the additional subsequent similarity measure value when calculating the subsequent similarity measure value. This is in analogy to the previous step, and comprises for example to calculate the sum or the (weighted) average of the subsequent similarity measure and the additional subsequent similarity measure.

In this embodiment, an overall initial similarity measure is calculated for all pairs of one the simulated images and the initial real image and an overall subsequent similarity measure value is calculated for all pairs of one of the additional simulated images and the subsequent real image. Instead of a single additional simulated image, a plurality of additional simulated images can be calculated for a plurality of viewing directions which differ from the viewing direction of the best matching simulated image.

In another embodiment, the method involves calculating an additional initial similarity measure value for a pair of the initial real image and an additional simulated image having a viewing direction which differs from the viewing direction of the best matching simulated image by a known difference and calculating an additional subsequent similarity measure value for a pair of the subsequent real image and the additional simulated image. Those steps are identical to the previous embodiment. However, while the previous embodiment involves to calculate an overall initial similarity measure value and an overall subsequent similarity measure value, this embodiment involves to output the indication signal if a value which is calculated from the difference between the initial similarity measure value and the corresponding subsequent similarity measure value and the difference between the additional initial similarity measure value and the corresponding additional subsequent similarity measure value fulfills a predetermined criterion. In other words, a plurality of differences is calculated for a plurality of pairs of an (additional) similarity measure value and an (additional) subsequent similarity measure value and a new value is calculated from the plurality of differences and analyzed in order to determine whether or not the indication signal is to be output.

The present invention further relates to a program which, when running on a computer, causes the computer to perform the method steps of the method described above and/or a program storage medium on which the program is stored, in particular in a non-transitory form.

The present invention further relates to a system for monitoring the position of a patient, comprising a computer on which the aforementioned program is stored and/or run. The system is for example a medical treatment system, such as a radiotherapy or radiosurgery system, or a medical imaging system, such as an MR, CT or X-ray imaging system.

A position in space means a position relative to a defined reference, such as for example an origin of a co-ordinate system. The reference can for example be a global co-ordinate system, a co-ordinate system defined with respect to a room, such as an operating room or a treatment room, or a co-ordinate system defined with respect to a medical apparatus, such as a medical imaging apparatus or a medical treatment apparatus such as an ExacTrac® apparatus.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block X-ray radiation. To this end, the marker can be provided with a surface which has corresponding reflective properties or can be made of metal in order to block the X-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include X-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_v-mat.php and http://www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), X-ray tomography, magnetic resonance tomography (MRT or MRI), conventional X-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of irradiating a patient with a treatment beam. More particularly, the invention does not involve or in particular comprise or encompass any surgical or therapeutic activity. The invention is instead directed as applicable to analyzing image date of the patient's body. For this reason alone, no surgical or therapeutic activity and in particular no surgical or therapeutic step is necessitated or implied by carrying out the invention.

In the following, the invention is described with reference to the enclosed figures which represent preferred embodiments of the invention. The scope of the invention is not however limited to the specific features disclosed in the figures, which show.

Figure 1:
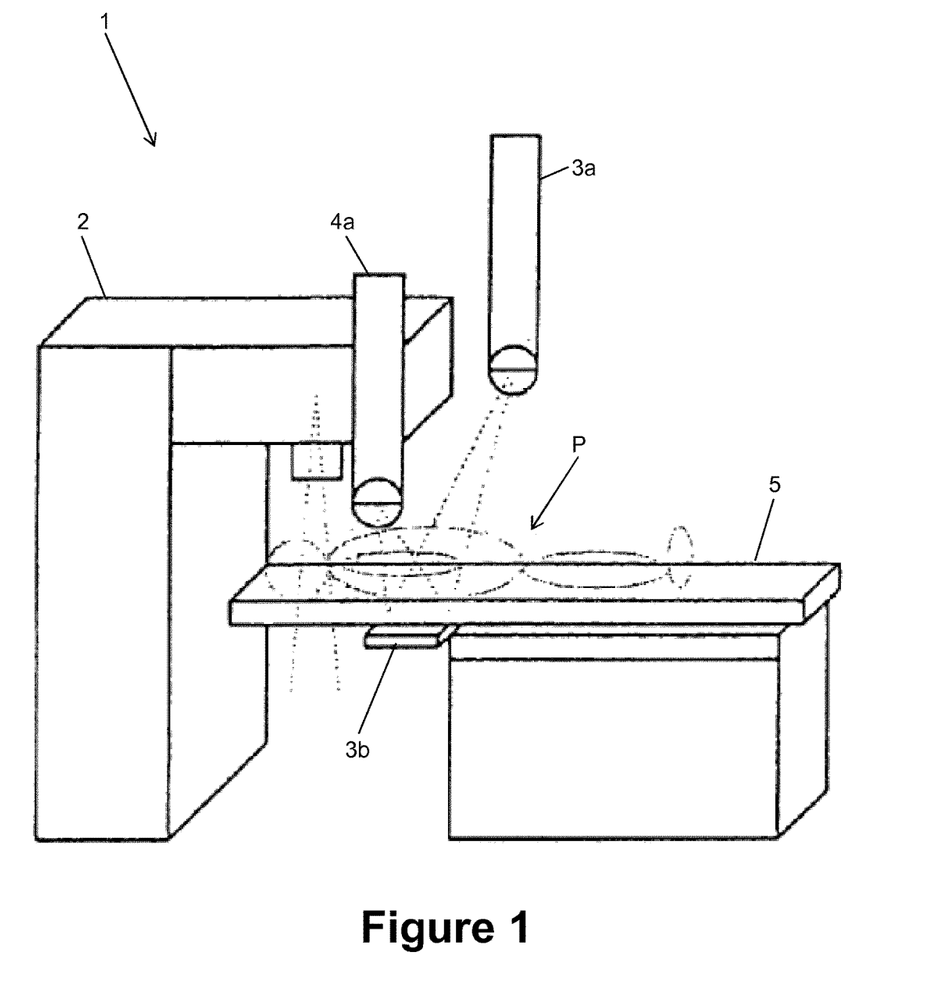
FIG. 1 a radiotherapy system.

FIG. 1 schematically shows the structure of a radiotherapy system 1, such as an ExacTrac® system sold by the applicant. The system 1 comprises a treatment beam generator 2 which irradiates a treatment beam onto a patient P. The treatment beam generator 2 optionally includes a rotatable gantry such that the origin of the treatment beam rotates about a defined axis, which in FIG. 1 is a horizontal axis. During rotation of the gantry, the treatment beam takes different paths through the body of the patient P, wherein it always irradiates an area which lies on the axis of rotation of the gantry. This area, which is also referred to as isocenter of the treatment beam generator 2, accumulates the irradiated dose, while tissue surrounding this area accumulates a lower dosage due to the rotation of the gantry. The position of the treatment beam generator 2, and optionally its axis of rotation, in space is known, or it defines a reference for the space in which other components are arranged.

The system 1 further comprises two X-ray imaging systems 3, 4 comprising X-ray sources 3a and 4a and X-ray detectors, wherein FIG. 1 only shows the X-ray detector 3b corresponding to the X-ray source 3a. The positions of the X-ray sources 3a, 4a and the X-ray detectors 3b in space are also known.

The system 1 further comprises a couch 5 which supports the patient P. The position of the couch 5 in space is optionally adjustable.

Figure 2:
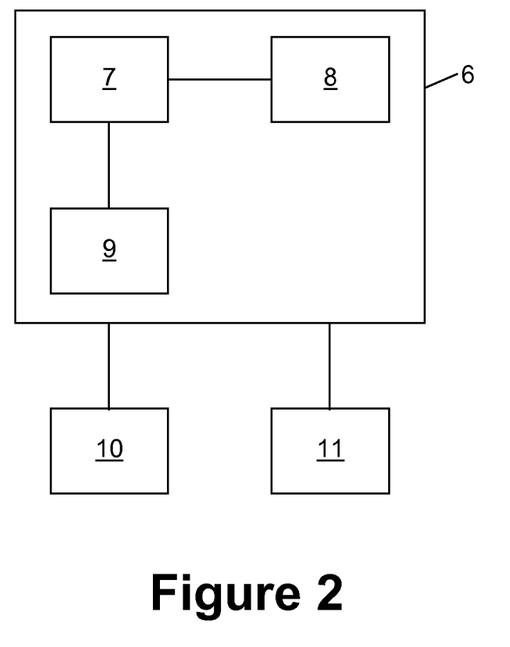
FIG. 2 a computer of the system of FIG. 1.

The radiotherapy system 1 further includes a computer 6 as shown in FIG. 2. This computer comprises a central processing unit 7, a storage unit 8 and an interface 9. The computer 6 is connected to an input device 10, such as a keyboard, a mouse, a touch screen, and to an output device 11 such as a monitor.

As outlined above, it is essential to exactly position the patient P relative to the radiotherapy system 1 such that the target area in the patient P lies in the isocenter of the treatment beam generator 2. Positioning the patient P can be performed by use of the radiotherapy system 1 or an external system, such as a system using optical or electromagnetic markers attached to a patient P. In the following, the desired position of the patient P in space, and therefore relative to the treatment beam generator 2 of the radiotherapy system 1 (subsequently abbreviated to the radiotherapy system 1), is also referred to as the initial position of the patient P.

Figure 3:
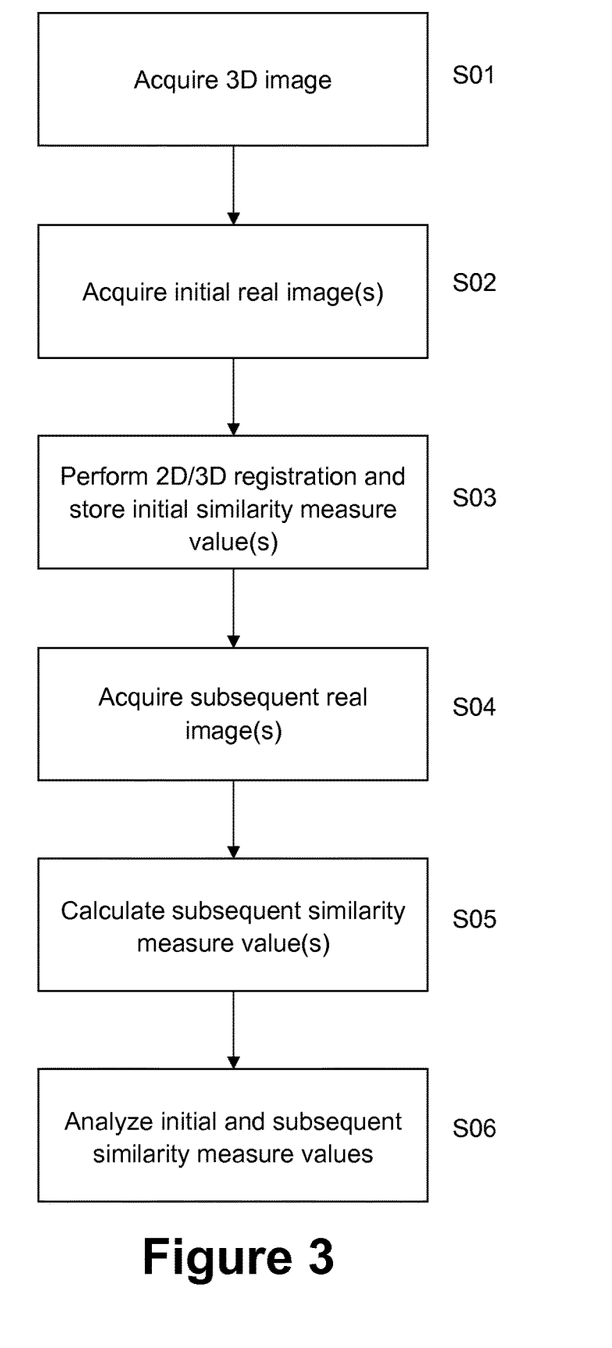
FIG. 3 a flow diagram of a process for monitoring the position of a patient.

The process of monitoring the position of a patient is now explained with reference to FIG. 3. The method steps of the present invention are performed by the computer 6, in particular by the central processing unit 7. A program which instructs the central processing unit 7 to perform the method steps is stored in the storage unit 8. The storage unit 8 may further store the data which are to be processed or have been processed by the central processing unit 7, such as real images, simulated images or a 3D image dataset. When data are acquired, this is typically done by or via the interface 9. Real images are for example acquired from the X-Ray imaging systems 3, 4 via the interface 9. In addition, control of the treatment beam generator is performed via the interface 9.

Step S01 involves acquiring a 3D image, represented by a 3D image dataset, of the patient P, which includes a 3D image which only shows a part of the patient P.

Step S02, which is performed when the patient P is in his or her initial position, involves acquiring initial real images. In the present embodiment, two initial real images of the patient P are acquired from the medical imaging systems 3 and 4. Those two initial real images show at least a part of the patient P which is identical or overlaps with the part of the patient P which is shown in the initial 3D image.

Step S03 involves performing 2D/3D registration and storing initial similarity measure values. In the 2D/3D registration, two simulated images are calculated which match the two initial real images acquired in step S02 best. A simulated image is calculated from the 3D image dataset for a particular (virtual) viewing direction on the 3D image dataset. As explained above, the two X-ray imaging systems 3 and 4 have a known and fixed location in space, and therefore known viewing directions in space. This means that the two viewing directions of the two X-ray imaging systems 3 and 4 have a known spatial relationship. During the 2D/3D registration, the same spatial relationship is assumed for the viewing directions of the simulated images. The virtual imaging systems, which would generate the simulated images if they would virtually image the 3D image dataset, thus emulate the X-ray imaging systems 3 and 4.

The 2D/3D registration of this exemplary embodiment virtually places the 3D image dataset in space such that a target area marked in the 3D image dataset, for example during treatment planning, is located at the isocenter of the treatment beam generator 2. The virtual imaging systems are virtually positioned at the positions of the X-ray imaging systems 3 and 4. A first pair of simulated images is then calculated from the 3D image dataset and the viewing directions of the simulated images onto the 3D image dataset as defined by the position of the 3D image dataset and the virtual imaging systems in space. Two initial similarity measure values are then calculated by respectively comparing one of the two initial real images with the corresponding one of the simulated images, wherein an initial similarity measure value represents the similarity between those two images. Algorithms for calculating similarity measure values are well-known, such as algorithms using a correlation coefficient, mutual information or a sum of squared differences. Then a joint initial similarity measure value is calculated from the two similarity measure values, for example by averaging the two similarity measure values.

Calculating a pair of simulated images from the 3D image dataset is then repeated for different positions of the 3D image dataset in space, thus resulting in a different joint initial similarity measure values. A suitable search strategy over possible positions of the 3D image dataset is implemented in order to maximize the joint initial similarity measure value. The pair of simulated images which results in the optimized joint initial similarity measure value are stored as stored simulated images. In addition, the joint initial similarity measure value is stored or the respective initial similarity measure values are stored separately.

Optionally, an offset is stored which represents the relative position between the initial position of the 3D image dataset and the position of the 3D image dataset for which the simulated images match the two initial real images best, that is result in the highest joint initial similarity measure value.

Optionally, step S03 involves outputting a synthesized image on the output device 11. The synthesized image preferably is an overlay of an initial real image and the corresponding simulated image. An operator can then look at the synthesized image to decide whether or not the 2D/3D registration was successful and input corresponding information via the input device 10. If the input information indicates that the 2D/3D registration was not successful, preferably a new 2D/3D registration is triggered.

Step S04 involves acquiring subsequent real images. In the present embodiment, two subsequent real images are acquired from the X-ray imaging systems 3 and 4.

Step S05 involves calculating subsequent similarity measure values. In the present embodiment, two subsequent similarity measure values are calculated, one subsequent similarity measure value for each pair of a subsequent real image and a corresponding stored simulated image. A joint subsequent similarity measure value is then calculated from the two subsequent similarity measure values, for example by averaging the two subsequent similarity measure values, preferably like the two initial similarity measure values are averaged. As an alternative, the two subsequent similarity measure values are individually compared to the stored initial similarity measure values.

Step S06 involves analyzing the initial and subsequent similarity measure values. In this embodiment, an absolute value of the difference between the initial similarity measure value stored in step S03 and the subsequent similarity measure value calculated in step S05 is calculated and compared to a threshold. If it exceeds the threshold, this indicates that the subsequent real images and the simulated images differ from each other by more than a predetermined margin, which indicates that the patient P has moved between the point in time at which the initial real images were taken and the point in time at which the subsequent real images were taken. An appropriate indication signal is then output, for example by use of the output device 11.

Optionally, step S03 involves calculating one or more additional initial similarity measure values, wherein each additional initial similarity measure value represents the similarity of an initial real image and a "displaced" simulated image. A displaced simulated image is calculated from the 3D image dataset for a viewing direction onto the 3D image dataset which is displaced, by a known displacement offset, from the viewing direction of the simulated image onto the 3D image dataset which results in the maximized initial similarity measure value. The displaced simulated images are stored along with the additional initial similarity measure values.

Step S05 then involves calculating additional subsequent similarity measure values for each pair of one of a displaced simulated image and the corresponding subsequent real image. The analysis in step S06 then does not only analyze the pair of the initial similarity measure value and the subsequent similarity measure value, but also the pairs of an additional initial similarity measure value and a corresponding additional subsequent similarity measure value. This approach knowingly compares "wrong" simulated images with the real images in order to obtain "displaced" similarity measure values. This makes the determination whether or not the patient has moved more robust. In a rare case in which a subsequent real image taken after a particular movement of the patient has a subsequent similarity measure value which is basically equal to the initial similarity measure value, this movement could not be detected by analyzing the initial and subsequent similarity measure values alone. However, it is very unlikely that the additional subsequent similarity measure values are also the same as the additional initial similarity measure values, such that the movement of the patient can be detected from the differences of the additional initial and subsequent similarity measure values.

The invention claimed is:

1. A computer implemented method for monitoring the position of a patient, comprising:
   acquiring a 3D image dataset of the patient;
   acquiring an initial real image of the patient from a medical imaging system having a known and fixed location in space, thus defining a known viewing direction of the initial real image in space, the real image being taken at a first point in time;
   performing 2D/3D registration by calculating a simulated image from the 3D image dataset which substantially matches the initial real image, the simulated image having a viewing direction onto the 3D image dataset;
   storing an initial similarity measure value for the pair of the initial real image and the calculated simulated image;
   acquiring a subsequent real image from the medical imaging system taken at a second point in time later than the first point in time;

calculating a subsequent similarity measure value for the pair of the subsequent real image and the calculated simulated image; and outputting an indication signal if the difference between the initial similarity measure value and the subsequent similarity measure value fulfills a predetermined criterion.

2. The method of claim 1, wherein
acquiring a plurality of initial real images of the patient from a plurality of medical imaging systems having a known and fixed location in space, thus defining known viewing directions of the initial real images in space, the plurality of real images being taken at the first point in time;

wherein performing the 2D/3D registration involves calculating a plurality of simulated images from the 3D image dataset which substantially match the initial real images, wherein there is one simulated image for each of the initial real images and each simulated image has a viewing direction onto the 3D image dataset;

storing a plurality of initial similarity measure values which comprises one similarity measure value for each pair of an initial real image and a corresponding simulated image;

acquiring a plurality of subsequent real images from the plurality of medical imaging systems taken at the second point in time;

calculating a plurality of subsequent similarity measure values for each pair of a subsequent real image and the corresponding calculated simulated image; and outputting the indication signal if a value which is calculated from the differences between the initial similarity measure values and the corresponding subsequent similarity measure values fulfills a predetermined criterion.

3. The method of claim 2, wherein the relations between the viewing directions of the simulated images equal the relations between the viewing directions of the real images.

4. The method of claim 2, wherein said value is calculated from all the differences or a subset of the differences.

5. The method of claim 1, wherein the real image is an X-ray image and the simulated image is a DRR image.

6. The method of claim 1, wherein the performing the 2D/3D registration involves positioning of the 3D image dataset in space, wherein a position of a virtual imaging system for calculating a simulated image equals the position of the corresponding medical imaging system in space.

7. The method of claim 6, wherein the 2D/3D registration is an iterative process starting with an initial position of the 3D image dataset in space, wherein this initial position is a position in which an isocenter defined with respect to the 3D image dataset equals an isocenter of a medical treatment beam.

8. The method of claim 7, wherein the difference between the initial position of the 3D image dataset and the adjusted position of the 3D image dataset is stored as an offset.

9. The method of claim 8, wherein, if the position of the patient has been changed, acquiring a new initial real images; performing a new 2D/3D registration with an initial position of the 3D image dataset calculated from the offset and the change in the patient's position; and storing a new initial similarity measure value.

10. The method of claim 1, further comprising stopping a treatment beam if the indication signal is output.

11. The method of claim 1, further comprising performing a new 2D/3D registration if the indication signal is output.

12. The method of claim 1, comprising the steps of:
calculating an additional initial similarity measure value for a pair of the initial real image and an additional simulated image having a viewing direction which differs from the viewing direction of the best matching simulated image by a known difference;

calculating an additional subsequent similarity measure value for a pair of the subsequent real image and the additional simulated image;

including the additional initial similarity measure value when calculating the initial similarity measure value; and including the additional subsequent similarity measure value when calculating the subsequent similarity measure value.

13. The method of claim 1, comprising the steps of:
calculating an additional initial similarity measure value for a pair of the initial real image and an additional simulated image having a viewing direction which differs from the viewing direction of the best matching simulated image by a known difference; and calculating an additional subsequent similarity measure value for a pair of the subsequent real image and the additional simulated image;

wherein the indication signal is output if a value which is calculated from the difference between the initial similarity measure value and the corresponding subsequent similarity measure value and the difference between the additional initial similarity measure value and the corresponding additional subsequent similarity measure value fulfills a predetermined criterion.

14. A non-transitory computer readable storage medium having a plurality of instructions for monitoring the position of a patient which, when executed by at least one processor, causes the at least one processor to:
acquire a 3D image dataset of the patient;
acquire an initial real image of the patient from a medical imaging system having a known and fixed location in space defining a known viewing direction of the initial real image in space, the real image being taken at a first point in time;

perform a 2D/3D registration by determining a simulated image from the 3D image dataset which substantially matches the initial real image, the simulated image having a viewing direction onto the 3D image dataset;

store an initial similarity measure value for the pair of the initial real image and the calculated simulated image;

acquire a subsequent real image from the medical imaging system taken at a second point in time later than the first point in time;

determine a subsequent similarity measure value for the pair of the subsequent real image and the calculated simulated image; and output an indication signal if the difference between the initial similarity measure value and the subsequent similarity measure value fulfills a predetermined criterion.

15. A system including memory and one or more processors operable to execute instructions, stored in the memory, including instructions to perform the operation of:
acquiring a 3D image dataset of the patient;
acquiring an initial real image of the patient from a medical imaging system having a known and fixed location in space and a known viewing direction taken at a first point in time;

performing a 2D/3D registration by calculating a simulated image from the 3D image dataset, the simulated image having a viewing direction onto the 3D image dataset;

storing an initial similarity measure value for the pair of the initial real image and the calculated simulated image;

acquiring a subsequent real image from the medical imaging system taken at a second point in time;

calculating a subsequent similarity measure value for the pair of the subsequent real image and the calculated simulated image; and outputting an indication signal if the difference between the initial similarity measure value and the subsequent similarity measure value fulfills a predetermined criterion.

\* \* \* \* \*